United States Patent
Herrmann et al.

(10) Patent No.: US 10,610,330 B2
(45) Date of Patent: Apr. 7, 2020

(54) PREFORMED DENTAL COMPOSITE CROWN, PROCESS OF PRODUCTION AND USE THEREOF

(71) Applicant: 3M INNOVATIVE PROPERTIES COMPANY, St. Paul, MN (US)

(72) Inventors: Andreas Herrmann, Munich (DE); Gallus Schechner, Herrsching (DE); Reinhold Hecht, Kaufering (DE); Helmar B. Mayr, Kaufering (DE); Malte Korten, Moorenweis (DE); Bernhard Hofmann, Peissenberg (DE); Gioacchino Raia, Turkenfeld (DE); Till Meurer, Bonn (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/078,455

(22) PCT Filed: Feb. 22, 2017

(86) PCT No.: PCT/US2017/018856
§ 371 (c)(1),
(2) Date: Aug. 21, 2018

(87) PCT Pub. No.: WO2017/155692
PCT Pub. Date: Sep. 14, 2017

(65) Prior Publication Data
US 2019/0021815 A1    Jan. 24, 2019

(30) Foreign Application Priority Data
Mar. 7, 2016  (EP) ..................................... 16158959

(51) Int. Cl.
*A61C 5/73*   (2017.01)
*A61C 13/087*   (2006.01)
(Continued)

(52) U.S. Cl.
CPC .................. *A61C 5/73* (2017.02); *A61C 5/77* (2017.02); *A61C 13/087* (2013.01); *A61C 13/20* (2013.01); *A61K 6/09* (2013.01)

(58) Field of Classification Search
CPC ........... A61C 5/73; A61C 5/77; A61C 13/087; A61C 13/20; A61K 6/09
See application file for complete search history.

(56) References Cited

U.S. PATENT DOCUMENTS 3,347,954 A   10/1967   Bredereck
3,541,068 A   11/1970   Taylor
(Continued)

FOREIGN PATENT DOCUMENTS

EP         2167013         3/2010
WO     WO 2001-30304       5/2001
(Continued)

OTHER PUBLICATIONS

International Search Report for PCT International Application No. PCT/US2017/018856, dated May 2, 2017, 5 pages.

*Primary Examiner* — Ralph A Lewis
(74) *Attorney, Agent, or Firm* — 3M IPC; Melissa E. Buss

(57) ABSTRACT

The invention relates to a preformed dental composite crown being characterized by its shape and chemical composition, the shape being characterized as follows: having an occlusal top surface and depending buccal, mesial, distal and lingual side surfaces, the side surfaces being connected to each other and forming a crown cervix, the wall thickness of the crown at the crown cervix being lower than 0.6 mm; at least two of opposing depending side surfaces having a concave shape; the chemical composition of the material the preformed dental composite crown is made of being a hardened composition comprising the following components: nano-filler(s) in an amount from 20 to 70 wt. %, resin matrix (Continued)

in an amount from 20 to 75 wt. %, wt. % with respect to the weight of the chemical composition, the resin matrix comprising urethane(meth)acrylate(s) and (meth)acrylate(s) not comprising a urethane moiety. The invention also relates to a kit of parts comprising such a preformed dental composite crown, processes for producing such crowns and the use of such a crown for treating a dental tooth.

15 Claims, 3 Drawing Sheets

(51) Int. Cl.
*A61C 13/20* (2006.01)
*A61K 6/09* (2006.01)
*A61C 5/77* (2017.01)

(56) References Cited

U.S. PATENT DOCUMENTS

| | | |
|---|---|---|
| 4,071,124 A | 1/1978 | Price |
| 4,443,587 A | 4/1984 | Schmitt |
| 4,544,742 A | 10/1985 | Schmitt |
| 4,642,126 A | 2/1987 | Zador |
| 4,652,274 A | 3/1987 | Boettcher |
| 4,737,593 A | 4/1988 | Ellrich |
| 4,795,823 A | 1/1989 | Schmitt |
| 6,572,693 B1 | 6/2003 | Wu |
| 6,653,375 B2 | 11/2003 | Moszner |
| 6,730,156 B1 | 5/2004 | Windisch |
| 6,899,948 B2 | 5/2005 | Zhang |
| 6,936,642 B2 | 8/2005 | Lehmann |
| 7,141,616 B2 | 11/2006 | Hecht |
| 8,003,040 B2 | 8/2011 | El-Siblani |
| 8,329,776 B2 | 12/2012 | Hecht |
| 8,651,867 B2 | 2/2014 | Zilberman |
| 2003/0008967 A1 | 1/2003 | Hecht |
| 2004/0161726 A1 | 8/2004 | Saito |
| 2007/0196792 A1 | 8/2007 | Johnson |

FOREIGN PATENT DOCUMENTS

| | | |
|---|---|---|
| WO | WO 2007-098485 | 8/2007 |
| WO | WO 2008-033758 | 3/2008 |
| WO | WO 2009-151957 | 12/2009 |
| WO | WO 2015-006087 | 1/2015 |

~300μm

PREFORMED DENTAL COMPOSITE CROWN, PROCESS OF PRODUCTION AND USE THEREOF

FIELD OF THE INVENTION

The present invention relates to hardened preformed dental composite crowns, a kit of parts containing those crowns, process of production and use thereof. The preformed dental crowns are in particular useful for treatment of pediatric dental defects.

BACKGROUND

For treating dental maladies a variety of different solutions are meanwhile on the market.

Generally, the dental maladies can be treated by restorative methods or prosthetic methods.

Prosthetic methods are typically used, if not sufficient remaining tooth structure is left which allows a restorative treatment, e.g. by filling a cavity with a dental filling material.

The prosthetic treatment usually starts with taking a dental impression from the dental situation in the mouth of the patient. The obtained record represents the status as is.

In a next step the tooth to be treated is further prepared, i.e. the tooth is shaped to a form which later allows the fixation of an artificial crown.

The artificial crown is typically designed from the information obtained from the dental impression and the shape of the treated tooth.

In a next step, the artificial crown is produced in a dental lab and specifically designed for this individual case. This procedure takes time and is expensive.

If, however, a fast and cheap prosthetic treatment is desired, the practitioner might consider using preformed crowns instead. This kind of treatment is often used in pediatric dentistry.

Different prefabricated crown types are meanwhile available on the market for this purpose.

The most commonly used solution is the stainless steel crown (e.g. from 3M Oral Care; 3M ESPE). Not only that stainless steel crowns are reasonable inexpensive to manufacture, they are also durable over years.

Preformed crowns made from stainless steel have in addition the benefit that they are pre-trimmed, belled and crimped for fast and easy placement. Due to a so-called "snap-on" feature, the stainless steel crown is readily retained and fits over the contour of the prepared tooth.

However, due to its metal surface, stainless steel crowns do not meet the desired aesthetic requirements.

To cure this defect, veneered stainless steel crowns have been suggested.

However, veneered stainless steel crowns show only a limited flexibility due to stiffer walls, at least at some areas of the crown. Moreover chipping of the veneering of these crowns is reported and a metallic shine of the underneath stainless steel crown lowers the esthetic appearance.

Thus, it was suggested to try to manufacture preformed crowns out of other materials.

Zirconia ceramic ($ZrO_2$) is quite common for individually designed crowns for esthetic dentistry. $ZrO_2$ has a couple of unique material properties, e.g. extremely high strength and toughness, translucency, stainability and biological compatibility, which makes it well suitable for crowns or even bridges. Therefore, it is no surprise that meanwhile also preformed zirconia crowns are available on the market.

However, due to material properties, the side walls of these crowns are not flexible and therefore no undercut design is possible. Further, compared to the stainless steel crowns, a different and more invasive tooth preparation without or with a very limited possibility of undercut retention is needed, which leads again to a more careful cementation technique. Solutions of roughening the inner surface of the crown, e.g. sandblasting or surface retention structure should help to support the cementation of the crown, but in sum could not replace the undercut feature.

It has also been suggested to manufacture preformed crowns out of polymer materials.

In this respect, U.S. Pat. No. 8,651,867 B2 (Zilberman) describes a dental crown configured to be readily mountable in a patient's mouth as part of a treatment of primary teeth and permanent molars, the dental crown having a natural appearance and color of a vital tooth and consisting of a thermoplastic material layer configured to define a tooth shaped top surface and flexible side surfaces.

As suitable thermoplastic materials polymers selected from polyacetal, polyacrylate, polymethacrylate (PMMA), polyaryletherketone (PAEK), polyetherketon (PEK), polyetheretherketon (PEEK), polyetherimide (PEI), polyethersulfone (PES) and polysulfone (PSU) are suggested.

US 2004/0161726 A1 (Saito et al.) describes a crown prosthesis having wear resistance and an aesthetic property comprising a polymer of a mixture of a polymerizable compound having an unsaturated double bond, a filler and a polymerization initiator, and having an outer shape resembling a tooth and a space to be filled with a dental composite resin between an inner surface thereof and an abutment tooth.

However, the workflow needed for applying polymer material based preformed crowns does not really differ from the workflow needed for applying preformed zirconia crowns, even if a more flexible material is used.

The commercially available polymer based preformed crowns show wall thicknesses of more than 500 μm, which gives them not enough flexibility and therefore no undercut design options as an additional support for cementation.

The fact that the material properties do not allow thinner walls makes the walls a limiting factor for the design options.

To nevertheless ensure a sufficient adhesive fixation of these crowns to a prepared tooth surface, an adhesive cementation, ideally with pretreatment of the inner surface is recommended or required, even if surface roughening is applied. This makes the whole prosthetic procedure more complicated and expensive. Generally, for crowns and bridges different cementation techniques are available.

These can be divided into clusters like temporary cementation (e.g. RelyX™ TempNE/E from 3M Oral Care; 3M ESPE), conventional cementation (e.g. Ketac™ CEM or Ketac™ CEM Plus from 3M Oral Care; 3M ESPE), self-adhesive resin cementation (e.g. RelyX™ Unicem from 3M Oral Care; 3M ESPE) or adhesive resin cementation (e.g. RelyX™ Ultimate from 3M Oral Care; 3M ESPE).

In general, the cementation needs to be durable over the life time of the indication, which could be achieved either due to chemical bonding or mechanical retention or a combination thereof.

The choice of the used cement or the general cementation technique for a specific indication is therefore influenced by the material of the restoration, the indication itself, the preparation technique, but also cost and esthetic plays a role.

For a fast and easy chairside workflow with preformed crowns, e.g. pediatric dentistry a fast and easy cementation technique is not only desired but required.

For this reason for the fixation of stainless steel crowns conventional cementation techniques are used. Those cements do not only have an easier workflow, but also are cheaper than self-adhesive resin or adhesive resin cements. Moreover they are more moisture tolerant and robust against blood and saliva than self-adhesive or adhesive cements.

This technique is the dominating one in pediatric dentistry, due to the time saving chairside workflow and the fact, that an individually designed crown is not necessarily needed.

In the end, the broad use of this type of crowns is the result of its easy workflow at the dentist chair. This easy workflow is very important to shorten the chairside time.

One important factor to enable this easy workflow is the provision of a material which enables an undercut design of the crown in the marginal area, doable due to thin and therefore flexible side walls. Especially for primary molar teeth, an undercut design leads to an easy, fast and less invasive preparation technique of the tooth stump, which enables a so called snap-on effect of the crown to the stump.

The snap-on effect ensures also an easy placement of the crown. Moreover the undercut design and preparation technique results in a macroscopic mechanical retention of the crown, which supports the cementation of the crown significantly.

WO 2007/098485 A2 (Nusmile) describes a preformed dental crown with a center surface, a circumferential surface transitioning from and integral with the central surface wherein the circumferential surface includes a taper toward a gingival end and wherein said taper has a thickness ranging from 0 to 0.5 mm at a gingival edge to at least 1.0 mm proximate the transition to the center surface.

WO 2008/033758 A2 (3M) describes a solid dental crown including a self-supporting solid hardenable preformed dental crown having an external crown shape defined by an external crown shape defined by an external crown surface.

US 2007/0196792 A1 (Johnson et al.) describes a prefabricated dental crown being tooth colored and having an undercut. Materials which are said to be useful for manufacturing the prefabricated dental crown are thermoplastic resins such as polyacetal, polyacrylate, polyamide, polyaryletherketone, polyetheretherketone (PEEK), polyetherimide, etc.

However, none of the solutions suggested in the prior art is completely satisfying. All these types of crowns do have drawbacks from different aspects, mainly related to a more complex and time consuming workflow but also due to durability and/or esthetic.

DESCRIPTION OF INVENTION

Thus, it is an object of the invention to provide a preformed dental crown which can easily and securely be fixed on a prepared tooth, similar to a preformed dental crown made from stainless steel, but having better aesthetics.

Further, it is desirable that the fixation of the dental crown to a prepared tooth can be done with low efforts and at low cost, e.g. by using a resin modified glass ionomer cement kind of product.

At least one of the above mentioned objectives can be solved by a preformed dental crown as described in the present text and the related processes for production and use thereof.

Thus, according to one aspect the invention relates to a preformed dental composite crown being characterized by its shape and chemical composition, the shape being characterized as follows:
  for molars and premolars having an occlusal top surface and depending buccal, mesial, distal and lingual, respectively palatinal side surfaces,
  for anterior teeth and incisors having a distal top surface and depending labial, mesial, distal and lingual, respectively palatinal side surfaces,
  the wall thickness of the crown at the crown cervix being less than to 0.6 mm;
  at least two of opposing depending side surfaces having a concave shape;
the chemical composition of the material the preformed dental composite crown is made of being a hardened composition and being characterized by comprising the following components:
  nano-filler(s): in an amount from 20 to 70 wt. %,
  resin matrix in an amount from 20 to 75 wt. %,
  the resin matrix comprising the polymerization product of
    a urethane(meth)acrylate(s) having at least 2 polymerizable moieties and
    a (meth)acrylate(s) having at least 1 or 2 polymerizable moieties but not comprising a urethane moiety,
  wt. % with respect to the weight of the chemical composition.

According to another aspect the invention relates to processes of production of preformed dental composite crowns as described in the present text applying either of the following technologies: additive manufacturing technology, molding technology, milling the preformed dental composite crown out of a milling block.

The invention is also directed to a kit of parts comprising a set of preformed dental crowns as described in the present text.

The preformed dental composite crown described in the present text is in particular useful to treat pediatric dental diseases.

DETAILED DESCRIPTION

FIG. 1 shows an example of a preformed dental composite crown placed on a tooth model.

FIG. 2 exemplifies how the undercut of the preformed dental composite crown can be determined.

Figure 1:
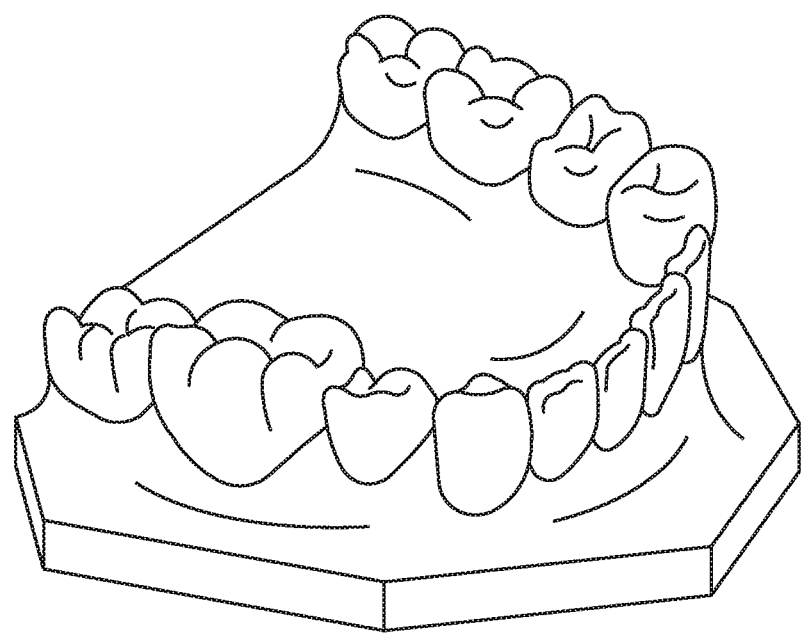

Unless defined differently, for this description the following terms shall have the given meaning:

A "hardenable component or material" or "polymerizable component" is any component which can be cured or solidified e.g. by heating to cause polymerization, chemical crosslinking, radiation-induced polymerization or crosslinking by using a redox initiator. A hardenable component may contain only one, two, three or more polymerizable groups. Typical examples of polymerizable groups include unsaturated carbon groups, such as a vinyl group being present i.a. in a (methyl)acrylate group.

An "initiator" is a substance being able to start or initiate the curing process of a hardenable composition.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i.e., $CH_2$=CH—C(O)—O—) and/or a methacryloxy group (i.e., $CH_2$=C($CH_3$)—C(O)—O—).

A "curing, hardening or setting reaction" is used interchangeable and refers to a reaction wherein physical properties such as viscosity and hardness of a composition changes over the time due to a chemical reaction between the individual components.

A "polymerizable component comprising an acidic group" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3$H or sulfinic acid residues such as —$SO_2$H.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

A "nano-filler" is a filler, the individual particles thereof have a size in the region of nanometers, e.g. an average particle diameter of less than about 200 nm or less than about 100 nm or less than about 50 nm. Useful examples are given in U.S. Pat. Nos. 6,899,948 and 6,572,693, the content of which especially with regard to nano-sized silica particles is herein incorporated by reference.

The measurement of the size of nano-particles is preferably based on a TEM (transmission electron microscopy) method, whereby a population is analyzed to obtain an average particle diameter. A preferred method for measuring the particle diameter can be described as follows:

Samples with a thickness not exceeding 80 nm are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

"Agglomerated" is descriptive of a weak association of particles usually held together by charge or polarity and can be broken down into smaller entities. The specific surface of agglomerated particles does not essentially deviate from the specific surface of the primary particles the agglomerate is made of (cf. DIN 53206; 1972).

Agglomerated fillers are commercially available e.g. from Degussa, Cabot Corp or Wacker under the product designation Aerosil™, CAB-O-SIL™ and HDK.

A "non-agglomerated filler" means that the filler particles are present in the resin in a discrete, un-associated (i.e. non-agglomerated and non-aggregated) stage. If desired this can be proven by TEM microscopy.

Non-agglomerated nano-sized silicas are commercially available e.g. from Nalco Chemical Co. (Naperville, Ill.) under the product designation NALCO COLLOIDAL SILICAS e.g. NALCO products #1040, 1042, 1050, 1060, 2327 and 2329.

Non-agglomerated fillers are used and described e.g. in EP 2 167 013 B1 (3M). The content of this reference is herewith incorporated by reference.

"Aggregated," as used herein, is descriptive of a strong association of particles often bound together by, for example, residual chemicals treatment or partially sintering. The specific surface of aggregated particles is typically smaller than the specific surface of the primary particles the aggregate is made of (cf. DIN 53206; 1972).

Further breakdown of the aggregates into smaller entities may occur during a polishing step applied to the surface of a composition containing the aggregated filler but not during dispersing the aggregated particles in a resin.

Aggregated fillers and processes for the production and surface treatment thereof are described e.g. in WO 01/30304 and U.S. Pat. No. 6,730,156 (3M). The content of these references is herewith incorporated by reference. A "urethane group" is a group having the structure "—NH—CO—O—".

"Additive manufacturing" means processes used to make 3-dimensional articles. An example of an additive manufacturing technique is stereolithography (SLA) in which successive layers of material are laid down under computer control. The articles can be of almost any shape or geometry and are produced from a 3-dimensional model or other electronic data source. Other examples of additive manufacturing processes or techniques include 3d-printing.

By "milling block" is meant a solid block (3-dim article) of material from which a dental article, dental workpiece, dental support structure or dental restoration can or is to be machined. A dental milling block may have a size of 20 mm to 30 mm in two dimensions, for example may have a diameter in that range, and may be of a certain length in a third dimension. A block for making a single crown may have a length of 15 mm to 30 mm, and a block for making bridges may have a length of 40 mm to 80 mm. A typical size of a block as it is used for making a single crown has a diameter of about 24 mm and a length of about 19 mm. Further, a typical size of a block as it is used for making bridges has a diameter of about 24 mm and a length of about 58 mm. Besides the above mentioned dimensions, a dental milling block may also have the shape of a cube, a cylinder or a cuboid. Larger mill blocks may be advantageous if more than one crown or bridge should be manufactured out of one blank. For these cases, the diameter or length of a cylindrical or cuboid shaped mill block may be in a range of 100 to 200 mm, with a thickness being in the range of 10 to 30 mm.

"Resin modified glass ionomer cement" means a hardenable dental material comprising acid-reactive glass, polyacid, water, polymerizable components and initiator. Resin modified glass ionomer cements undergo a twofold curing reaction, a glass ionomer acid base based cement reaction and polymerization of typically (methacrylate) acrylate based monomers.

"Adhesive resin cement" means a hardenable dental material which cures by radical polymerization of polymerizable components (but not by a glass ionomer cement reaction). An adhesive resin cement requires a pre-treatment of the hard dental surfaces to effect adhesion. In contrast to resin modified glass ionomer cements, an adhesive resin cement does not contain added water.

A "self-adhesive resin cement" is an adhesive resin cement which in addition contains acidic components and thus does not require a pre-treatment of the hard dental surfaces to effect adhesion.

In contrast to resin modified glass ionomer cements, adhesive resin cement and self-adhesive resin cement typically only cure by polymerization reaction.

"Ambient conditions" mean the conditions which the inventive composition is usually subjected to during storage and handling. Ambient conditions may, for example, be a pressure of 900 to 1100 mbar, a temperature of −10 to 60° C. and a relative humidity of 10 to 100%. In the laboratory ambient conditions are adjusted to about 23° C. and about 1013 mbar. In the dental and orthodontic field ambient conditions are reasonably understood as a pressure of 950 to 1050 mbar, temperature of 15 to 40° C. and relative humidity of 20 to 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.). Unless otherwise indicated, all numbers expressing quantities of ingredients, measurement of physical properties such as described below and so forth used in the specification and claims are to be understood as being modified in all instances by the term "about."

The preformed dental composite crown described in the present text has a couple of advantages.

The preformed dental composite crown can be used in a chairside workflows. As the crown is already provided in a ready for use shape, there is no need to have the dental crown produced in a separate step in a dental lab. This does not only save time for the patient but is also convenient for the practitioner.

Compared to preformed crowns made from stainless steel, the preformed dental composite crown described in the present text is much more aesthetic without negative impact on the overall workflow.

Compared to preformed dental crowns based on zirconia or thermoplastic material (e.g. PEEK), the shape of the preformed dental composite crown described in the present text can easily be further adapted by the practitioner, if desired, e.g. by cutting or grinding.

However, similar to preformed crowns made from stainless steel the preformed dental composite crown described in the present text shows a so-called "snap on effect". That is, the fitting of the crown on the prepared tooth can easily be checked before the crown is finally fixed.

Further, due to its flexible nature, the preformed dental composite crown can also be easily fixed to not optimally prepared tooth structures.

This "snap on effect" is basically the result of a) providing a crown with at least two opposing depending side surfaces, which have a concave shape, b) adjusting the wall thickness of the crown at the crown cervix less than 0.6 mm and c) manufacturing the crown from a material containing a hardened resin matrix comprising urethane(meth)acrylates.

A reduced wall thickness of the crown at the crown cervix is beneficial because it provides the crown with sufficient flexibility and allows an aesthetic marginal fit.

The preformed dental composite crown described in the present text shows also a couple of advantageous mechanical properties like sufficient flexural strength, fracture work, E-modulus and abrasion resistance.

The preformed dental composite crown can easily and reliably be cemented to a prepared tooth surface. As outlined above, in particular in pediatric dentistry the treatment of defect tooth structure needs to be fast and reasonable cheap. The costs for the cementation of the crown may not exceed the costs of the crown itself.

Surprisingly, it was found that the adhesive strength can be even improved, if a dental resin modified glass ionomer cement is used.

Without wishing to be bound to a certain theory, it is believed that using a cement containing polymerizable components with reactive moieties having a similar structure like those used for producing the preformed dental composite crown may be beneficial for improving the adhesion.

The preformed dental composite crown described in the present text can also easily be produced, either by milling out of a preformed composite block, by injection molding or by using a build-up technology (e.g. 3d-printing).

In summary, the preformed dental composite crown described in the present text provides excellent aesthetic, durability and an easy workflow during use similar to the process used for stainless steel crowns.

The preformed dental composite crown described in the present text has a particular shape.

The shape is characterized as follows: The preformed crown has a top surface and depending buccal, respectively labial, mesial, distal, lingual, respectively palatinal side surfaces.

The side surfaces are connected to each other and form a crown cervix. The lower region of the crown cervix forms the crown margin or crown rim.

The preformed crown has an outer and an inner surface. The inner surface is the surface to be attached to a prepared dental tooth.

The wall thickness of the preformed crown at the crown cervix (in a distance of 1 mm from the crown margin) is lower than 0.6 mm or in a range of 0.1 to 0.4 mm or 0.1 to 0.3 mm or 0.1 to 0.2 mm.

The wall thickness of the top surface (occlusal and/or distal) of the preformed crown is typically in the range of 0.15 mm to 1.5 mm or in the range of 0.4 mm to 1.0 mm.

At least two of the opposing and depending side surfaces of the preformed crown have a concave shape, preferably the buccal and lingual side surfaces. That is, the side walls of the preformed crown have a curved shape and thus provide an undercut in the region of the crown cervix.

If desired, the dimension of the undercut U in mm can be calculated by the formula $U=D2-D1$, wherein D1 is the distance of the opposing inner side walls having a concave shape of the preformed crown measured 1 mm above the crown cervix, if the preformed crown is cut into halves and wherein D2 is the maximum distance of said opposing inner side walls of the crown measured parallel to D1.

Figure 2:
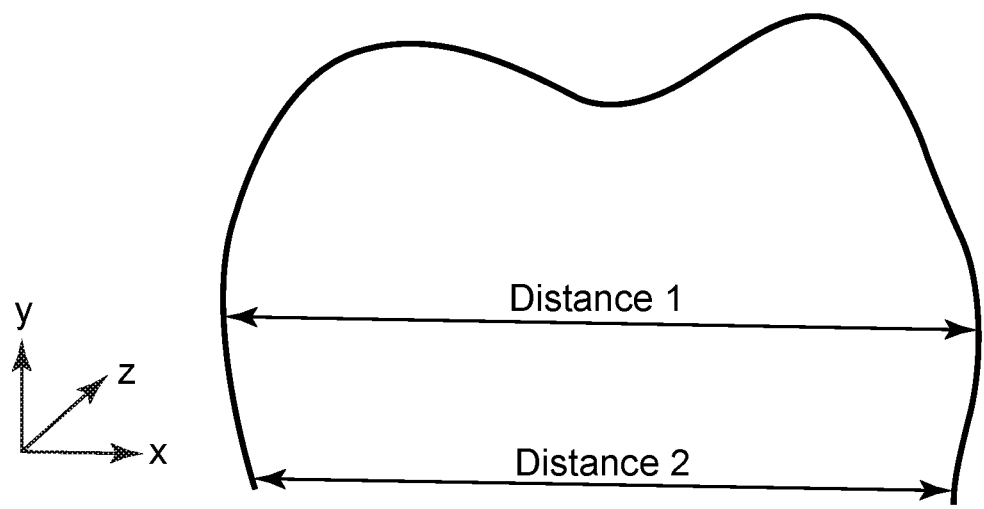

In FIG. 2 the respective distances D1 and D2 of the crown design in cross section are exemplified. The preformed dental composite crown has an x, y and z direction. The cross section is done in the middle of the crown in z-direction. The distance D1 is measured 1 mm in the direction of y from each crown margins. The distance D2 is measured parallel y-shifted to distance D1. Distance D2 is the largest distance of the crown in this cross section.

The undercut (U=d2−d1) of the preformed dental composite crown described in the present text is typically larger than 0.2 mm or 0.3 mm or 0.4 mm. A typical range is from 0.2 to 1.0 or from 0.3 to 0.8 mm.

In one embodiment, the shape of the preformed crown is further characterized by either of the following features alone or in combination:

The wall thickness of the side surfaces of the crown is typically not larger than 0.6 mm or 0.5 mm or 0.4 mm.

According to one embodiment, the wall thickness of the side surfaces of the preformed crown is in a range from 0.1 mm to 0.4 mm.

According to one embodiment, the inner surface of the preformed dental composite crown is roughened and/or has retention elements. This feature may help to enhance adhesion of the crown to the surface of a prepared dental tooth.

According to one embodiment, the outer surface of the preformed dental composite crown is polished.

Such a shape was proven to be beneficial to allow an easy fixation of the preformed crown on a prepared tooth stump.

Due to the low wall thickness, the preformed crown is sufficiently elastic to be placed on a prepared tooth stump, even if there is an undercut.

If the thickness of the side walls of the preformed crown is too large, the preformed crown is not sufficiently elastic. If the thickness of the side walls of the crown is too low, the preformed crown is not sufficiently robust.

This is also beneficial, if the fit of the preformed crown has to be tested before cementation and the preformed crown has to be removed from the prepared tooth stump for application of the respective dental cement.

In general, the dentist typically wants a preformed dental composite crown to be as thin as possible. But depending on the chemical composition the preformed dental composite crown is made of, the durability, e.g. abrasion or even complete breakage of the crown limit the thickness to an appropriate level. On the other hand the flexibility of the wall thickness will decrease with an increasing wall thickness.

It was found that a wall thickness as described in the present text provides the required flexibility to provide the preformed crown with the desired snap-on effect.

A perspective figure of a preformed dental composite crown as described in the present text is shown in FIG. 1. The preformed dental composite crown (molar) is placed on a tooth stump of an artificial dental arch.

Figure 3:
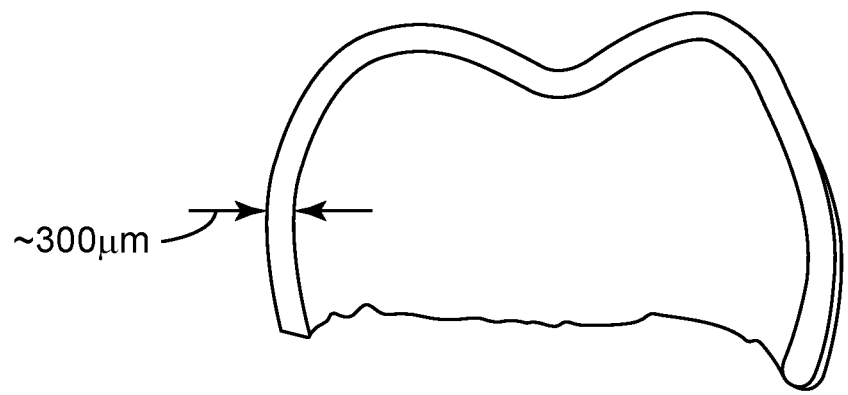
FIG. 3 shows the shape of the preformed dental composite crown used for conducting the adhesive experiments in cross section.

In FIG. 3 a schematic cross section of an embodiment of a preformed dental composite crown as described in the present text is shown. The crown wall has a thickness of about 300 μm.

If desired, the preformed dental composite crown described in the present text can be characterized by mechanical properties of the hardened chemical composition the composite crown is made of.

Typically, the chemical composition can be characterized by one or more or all of the following parameters:

flexural strength: from 50 to 200 MPa or from 80 to 150 MPa determined according to ISO 4049:2009;

E-modulus: from 1,000 to 4,000 MPa determined according to ISO 4049:2009 in combination with DIN EN 843-2:2007;

impact strength: from 5 to 15 kJ/m$^2$ determined according to DIN 53453:175-05;

abrasion: less than 20 or less than 15 or less than 10 mm$^3$ (determined as described in the example section);

color: being tooth colored.

The combination of the following features is often preferred: high impact strength combined with low abrasion.

A sufficient flexural strength is beneficial because the material of the crown will not break easily.

A sufficient low E-modulus is beneficial because the material of the crown has a sufficient flexibility.

A sufficient impact strength is beneficial because the material of the crown has a high toughness and can resist to fracture.

A sufficient abrasion is beneficial because the crown will not abrade and maintain its anatomical shape during chewing.

The preformed dental composite crown described in the present text is also characterized by its chemical composition. The chemical composition is not a hardenable chemical composition, but a hardened (i.e. cured) chemical composition.

The chemical composition, the preformed dental composite crown is made of, comprises nano-filler(s).

The nano-filler(s) can be selected from aggregated, agglomerated or discrete (i.e. non-agglomerated, non-aggregated) nano-sized particles or mixtures thereof.

It was found that compared to other fillers, using nano-filler(s) is beneficial because it allows for the formulation of a composition with high filler load resulting in better mechanical properties, e.g. polishability or abrasion and in higher aesthetics.

According to one embodiment, the nano-filler(s) comprises aggregated nano-sized particles.

The nano-filler comprising aggregated nano-sized particles can typically be characterized by at least one or all of the following features:

Specific surface: from 30 to 400 or from 60 to 300 or from 80 to 250 m$^2$/g, comprising particles of $SiO_2$, $ZrO_2$, $Al_2O_3$ and mixtures thereof.

If desired, the specific surface can be determined according to Brunauer, Emmet and Teller (BET) by using a device (Monosorb™) available from Quantachrome.

If desired, the mean particle size can be determined by light scattering using e.g. a Malvern Mastersizer 2000 device available from Malvern Instruments.

A suitable nano-filler comprising aggregated nano-sized particles can be produced according to the processes described e.g. in U.S. Pat. No. 6,730,156 (preparatory example A).

A useful nano-filler comprising aggregated nano-sized particles can be prepared from a suitable sol and one or more oxygen containing heavy metal compound solution(s) precursors which may be salts, sols, solutions, or nano-sized particles; of these, sols are preferred. For purposes of this invention, a sol is defined as a stable dispersion of colloidal solid particles within a liquid. The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc. Factors that will guide the choice of the sol depends on the combination of the following properties: a) the average size of the individual particles, which is preferably less than 100 nm in diameter, b) the acidity: the pH of the sol should be preferably below 6 and more preferably below 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability of a dental restoration made out of a composite comprising such nanoparticles.

If the starting sol is basic, it should be acidified e.g. by addition of nitric or other suitable acid to decrease the pH. However choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio ranges of non-heavy metal oxide ("non-HMO") to heavy metal oxide ("HMO"), expressed as non-HMO:HMO is 0.5:1 to 10:1, more preferably 3:1 to 9:1, and most preferable 4:1 to 7:1.

In a preferred embodiment where the aggregated nano-sized particles contain silica and zirconium containing compounds, the method of preparation starts with a mixture of silica sol and zirconyl acetate, at about a 5.5:1 molar ratio.

Prior to mixing the non-heavy metal oxide sol with the heavy metal oxide precursor, the pH of the non-heavy metal oxide sol is preferably reduced to provide an acidic solution having a pH of 1.5 to 4.0.

The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying.

The resulting dried material is preferably made up of small substantially spherical particles as well as broken hollow spheres. These fragments are then batch calcined to further remove residual organics. The removal of the residual organics allows the filler to become more brittle, which results in more efficient particle size reduction. During calcining, the soak temperature is preferably set at 200° C. to 800° C., more preferably 300° C. to 600° C. Soaking is performed for 0.5 hours to 8 hours, depending on the amount of material being calcined. It is preferred that the soak time of the calcine step be such that a plateaued surface area is obtained. It is preferred that the time and temperature be chosen such that the resulting filler is white in color, free from black, grey, or amber colored particles, as determined by visual inspection.

The calcined material is then preferably milled to a median particle size of less than 5 µm, preferably less than 2 µm (on a volumetric basis), as can be determined by using a Sedigraph 5100 (Micrometrics, Norcross, Ga.). The particle size determination can be performed by first obtaining the specific density of the filler using an Accuracy 1330 Pycometer (Micrometrics, Norcross, Ga.). Milling can be accomplished by various methods including for example, stirred milling, vibratory milling, fluid energy milling, jet milling and ball milling. Ball milling is the preferred method.

The resulting fillers comprise, contain, consist essentially or consist of aggregated nano-sized particles. If desired, this can be proven by transmission electron microscopy (TEM).

If desired, the surface of the filler particles can be surface treated. The surface-treatment can be accomplished according to a process as described in U.S. Pat. No. 6,730,156 or WO 01/30304 or U.S. Pat. No. 6,730,156 (e.g. preparatory example B). The content of these references is herewith incorporated by reference.

Once dispersed in the resin, the filler remains in an aggregated stage. That is, during the dispersion step the particles do not break up into discrete (i.e. individual) and un-associated (i.e. non-aggregated) particles.

If present, the nano-filler comprising aggregated nano-sized particles is typically present in either of the following amounts:
at least 20 or at least 30 or at least 40 wt. % with respect to the weight of the chemical composition of the preformed dental composite crown.
utmost 70 or utmost 60 or utmost 50 wt. % with respect to the weight of the chemical composition of the preformed dental composite crown.
from 20 to 70 or from 30 to 60 or from 40 to 50 wt. % with respect to the weight of the chemical composition of the preformed dental composite crown.

According to one embodiment, the nano-filler(s) comprises agglomerated nano-sized particles.

Nano-filler(s) comprising agglomerated nano-sized particles are typically characterized by at least one or all of the following features:
Specific surface: (BET according to Brunauer, Emmet and Teller): from 30 to 400 or 50 to 300 or from 70 to 250 m$^2$/g;
comprising particles of $SiO_2$, $ZrO_2$, $Al_2O_3$ and mixtures thereof.

If desired, the specific surface can be determined as described above.

Suitable agglomerated nanoparticles include fumed silicas such as products sold under the tradename Aerosil™ e.g. Aerosil™ OX-130, -150, and -200, Aerosil™ R8200 available from Degussa AG, (Hanau, Germany), CAB-O-SIL™ M5 available from Cabot Corp (Tuscola, Ill.), and HDK™, e.g. HDK-H 2000, HDK H15; HDK H18, HDK H20 and HDK H30 available from Wacker.

The surface of the filler particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174 from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, cycloalkyl, hydroxy alkyl, aryl, hydroxy aryl, or amino alkyl functional silanes.

If present, the nano-filler comprising agglomerated nano-sized particles is typically present in either of the following amounts:
  at least 1 or at least 3 or at least 5 wt. % with respect to the weight of the chemical composition of the preformed dental composite crown;
  utmost 20 or utmost 15 or utmost 10 wt. % with respect to the weight of the chemical composition of the preformed dental composite crown.
  from 1 to 20 or from 3 to 15 or from 5 to 10 wt. % with respect to the weight of the chemical composition of the preformed dental composite crown.

According to one embodiment, the nano-filler(s) comprises discrete nano-sized particles.

Discrete nano-sized particles which can be used are preferably substantially spherical and substantially non-porous.

Nano-filler(s) comprising discrete nano-sized particles are typically characterized by at least one or all of the following features:
  Average particle diameter: less than 200 nm or less than 100 nm;
  comprising particles of $SiO_2$, $ZrO_2$ and mixtures thereof.

Preferred nano-sized silicas are commercially available from Nalco Chemical Co. (Naperville, Ill.) under the product designation NALCO™ COLLOIDAL SILICAS. For example, preferred silica particles can be obtained from using NALCO™ products 1040, 1042, 1050, 1060, 2327 and 2329.

If present, the discrete nano-sized particles are typically present either of the following amounts:
  at least 1 or at least 3 or at least 5 wt. % with respect to the weight of the chemical composition of the preformed dental composite crown;
  utmost 30 or utmost 25 or utmost 20 wt. % with respect to the weight of the chemical composition of the preformed dental composite crown.
  from 1 to 30 or from 3 to 25 or from 5 to 20 wt. % with respect to the weight of the chemical composition of the preformed dental composite crown.

According to one embodiment, the chemical composition of the preformed dental composite crown comprises:
  aggregated nano-sized particles in an amount from 20 to 70 wt. %,
  agglomerated nano-sized particles in an amount from 1 to 20 wt. %,
  discrete nano-sized particles in an amount from 1 to 30 wt. %.

The chemical composition of the preformed dental composite crown comprises a resin.

The resin is the polymerization product of urethane(meth)acrylate(s) having at least two polymerizable moieties and a (meth)acrylate(s) having at least one or two polymerizable moieties but not comprising a urethane moiety.

If a different chemical composition is chosen, the desired mechanical properties are typically not achieved.

The chemical composition of the preformed dental composite crown comprises at least one urethane(meth)acrylate with at least two polymerizable (meth)acrylate moieties.

If desired, the chemical composition may comprise at least two, three or four different kinds of urethane(meth)acrylate(s).

It was found that the addition of urethane(meth)acrylate(s) to the resin composition contributes to improve certain mechanical properties like E-modulus and fracture resistance of the cured resin composition.

In particular the urethane(meth)acrylate(s) described in the present text were found to be useful.

The molecular weight of the urethane(meth)acrylate is at least about 450 or at least about 800 or at least about 1,000 g/mol.

Useful ranges include from 450 to 3,000 or from 800 to 2,700 or from 1,000 to 2,500 g/mol.

Molecules having a molecular weight above about 450 g/mol or above about 1,000 g/mol are usually less volatile than molecules having a lower molecular weight and thus may contribute to providing a biocompatible composition.

Further, if the molecular weight is not sufficiently high, the desired fracture work of the hardended dental composition may not be achieved.

The urethane(meth)acrylates employed in the composition are typically obtained by reacting an NCO-terminated compound with a suitable monofunctional (meth)acrylate monomer such as hydroxyethyl acrylate, hydroxyethyl methacrylate, hydroxypropylmethacrylate, preferably hydroxyethyl- and hydroxypropylmethacrylate.

Urethane (meth)acrylates may be obtained by a number of processes known to the skilled person.

For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates.

Any of the known polyisocyanates such as alkyl and alkylene polyisocyanates, cycloalkyl and cycloalkylene polyisocyanates, and combinations such as alkylene and cycloalkylene polyisocyanates can be employed.

Preferably, diisocyanates having the formula $X(NCO)_2$ are used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an araliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocycanate, meta- and para-tetramethylxylene diisocycanate, 1,4-phenylene diisocyanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane(meth)acrylate compound. In general, any (meth)acrylate-type capping agent having a terminal hydroxyl group and also having an acrylic or methacrylic moiety can be employed, with the methacrylic moiety being preferred.

Examples of suitable capping agents include 2-hydroxyethyl(meth)acrylate, 2-hydroxypropyl (meth)acrylate, glycerol di(meth)acrylate and/or trimethylolpropane di(meth)acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Suitable examples of urethane (meth)acrylates include 7,7,9-trimethyl-4,13-dioxo-3,14-dioxa-5,12-diazahexadecane-1,16-dioxy-dimethacrylate (e.g. Plex 666-1, Röhm), 7,7,9-trimethyl-4,13-dioxo-5,12-diazahexadecane-1,16-dioxy-dimethacrylate (UDMA), urethane (methacrylates) derived from 1,4 and 1,3-Bis(1-isocyanato-1-methylethyl) bezene (e.g. as described in EP 0 934 926 A1) and mixtures thereof.

According to one embodiment, the urethane(meth)acrylate is characterized as follows:
having the structure A-(-S1-U-S2-MA)$_n$, with
A being a connector element comprising at least one unit,
S1 being a spacergroup comprising at least 4 units connected with each other,
S2 being a spacergroup comprising at least 4 units connected with each other,
the units of A, S1 and S2 being independently selected from $CH_3$—, —$CH_2$—, —O—, —S—, —$NR^1$—, —CO—, —$CR^1$=,

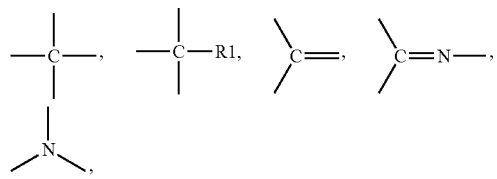

—N=, —$CR^1R^2$—, with $R^1$ and $R^2$ being independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups, U being a urethane group connecting spacergroups S1 and S2,
MA being an acrylate or methacrylate group and
n being 3 to 6.
According to one embodiment the urethane(meth)acrylate is represented by the structure

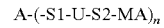

With
A being a connector element comprising at least about 1, 2, 3, 4, 5, 6, 7, 8, 9, 10, 11, 12, 13, 14, 15, 16, 17, 18, 19 or 20 units,
S1 being a spacergroup comprised of units connected with each other and comprising at least about 4, 5, 6, 7, 8, 9 or 10 units,
S2 being a spacergroup comprised of units connected with each other and comprising at least about 4, 5, 6, 7, 8, 9, 10, 12, 15, 20 or 25 units,
U being a urethane group connecting spacergroups S1 and S2,
MA being an acrylate or methacrylate group and
n being 3 to 6 or 4 to 6 or 5 to 6.
It can be preferred, if A has a cyclic structure and comprises at least about 6 units.
It can further be preferred, if S1 has a linear or branched structure and comprises at least about 4 or about 6 units.
It can further be preferred, if S2 has a linear or branched structure and comprises at least about 6 or about 8 units.
A urethane(meth)acrylate wherein A has a cyclic structure and comprises at least about 6 units and S1 has a linear structure and comprises at least about 4 units and S2 has a linear structure and comprises at least about 8 units and U is a urethane group can also be preferred.

Neither the atoms of the urethane group connecting S1 and S2 nor the atoms of the (meth)acrylgroup belong to the spacergroup S1 or S2. Thus, the atoms of the urethane group do not count as units of the spacergroups S1 or S2.

The nature and structure of the connector element is not particularly limited. The connector element can contain saturated (no double bonds) or unsaturated (at least one or two double bonds) units, aromatic or hetero aromatic units (aromatic structure containing atoms including N, O and S).

Specific examples of connector element A having a cyclic structure include:

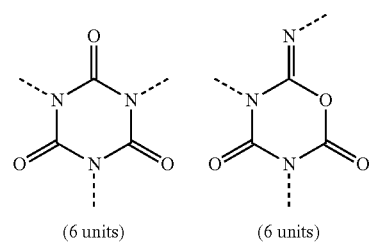

(6 units)          (6 units)

Specific examples of connector element A having a non-cyclic but branched structure include:

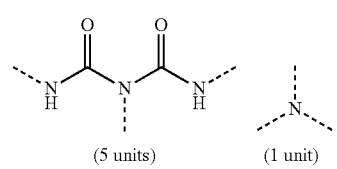

(5 units)          (1 unit)

-continued

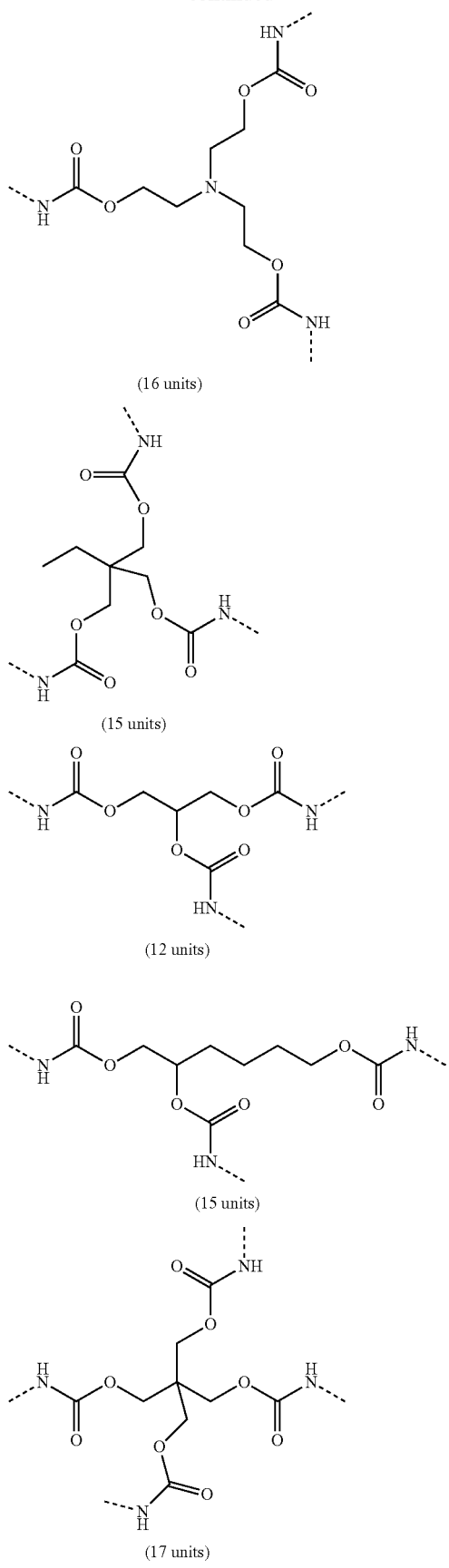

(16 units)

(15 units)

(12 units)

(15 units)

(17 units)

-continued

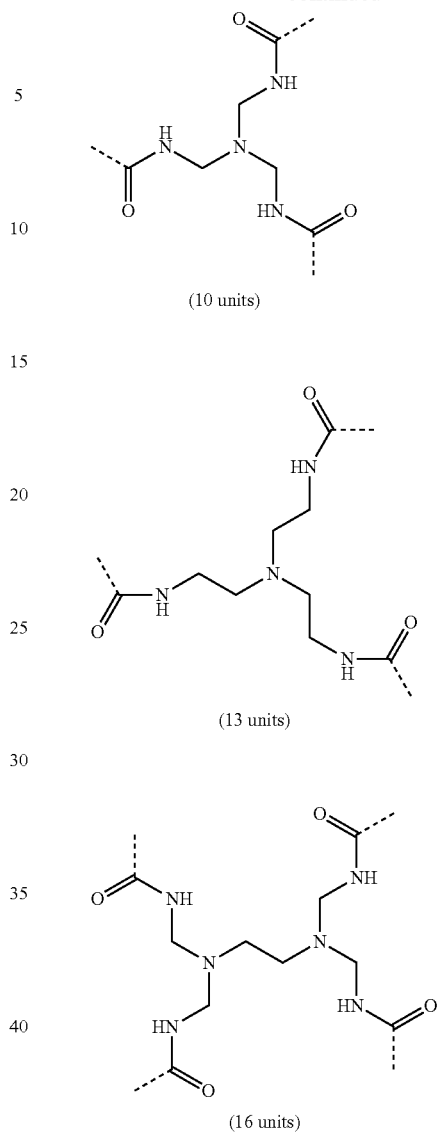

(10 units)

(13 units)

(16 units)

The dotted lines indicate the bondings to the spacergroup S1.

The nature and structure of the spacergroups S1 or S2 is not particularly limited, either.

The spacergroups are comprised of units connected with each other. Typical units include: $CH_3-$, $-CH_2-$, $-O-$, $-S-$, $-NR^1-$, $-CO-$, $-CR^1=$,

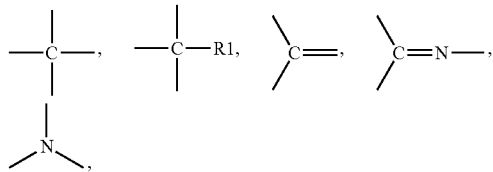

$-N=$, $-CR^1R^2-$, with $R^1$ and $R^2$ independently selected from hydrogen, alkyl, substituted alkyl, alkenyl, cycloalkyl, substituted cycloalkyl, arylalkyl, aryl or substituted aryl.

These units can form linear, branched or cyclic structures such as alkyl, cycloalkyl, aryl, ester, urethane or amide groups.

The structure of S1 can be identical to the structure of S2. However, in some embodiments the structure of S1 is different from S2. In a specific embodiment the number of units being present in S1 is less or equal than the number of units being present in S2.

In a specific embodiment, S1 may have a saturated hydrocarbon structure.

In another specific embodiment, S2 may have a saturated hydrocarbon structure.

Typical examples of useful spacer groups for S1 include:

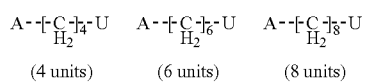
(4 units)    (6 units)    (8 units)

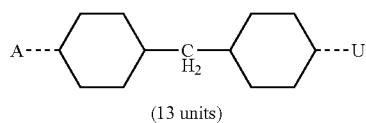
(13 units)

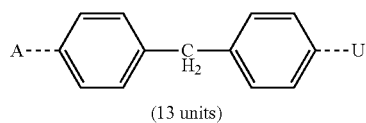
(13 units)

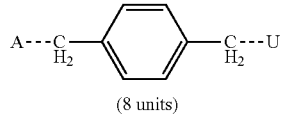
(8 units)

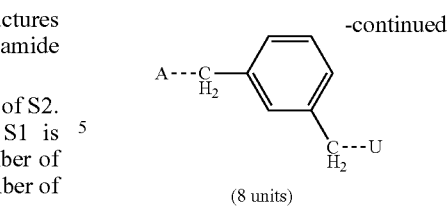
(8 units)

The dotted lines indicate the chemical bonding to either the group A or the group U.

Typical examples of useful spacer groups for S2 include:

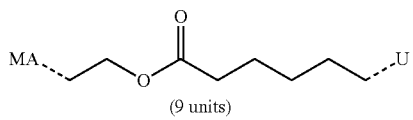
(9 units)

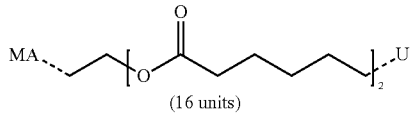
(16 units)

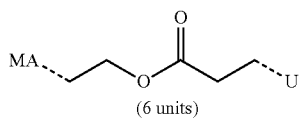
(6 units)

The dotted lines indicate the chemical bonding to either the (meth)acrylate group or the group U. The number of the units to be counted according to the invention is given in brackets.

Specific examples of hardenable component (A1) include

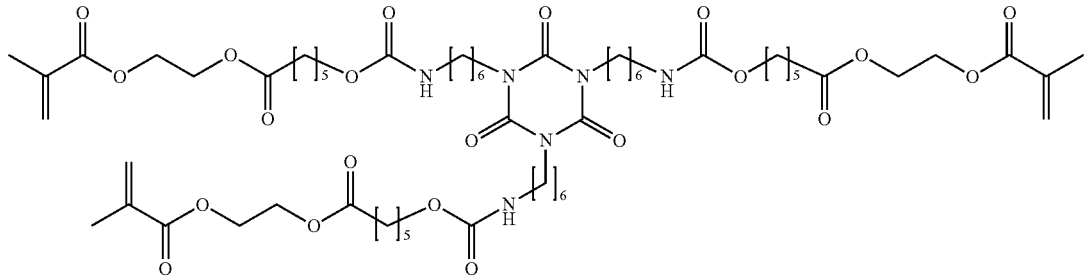

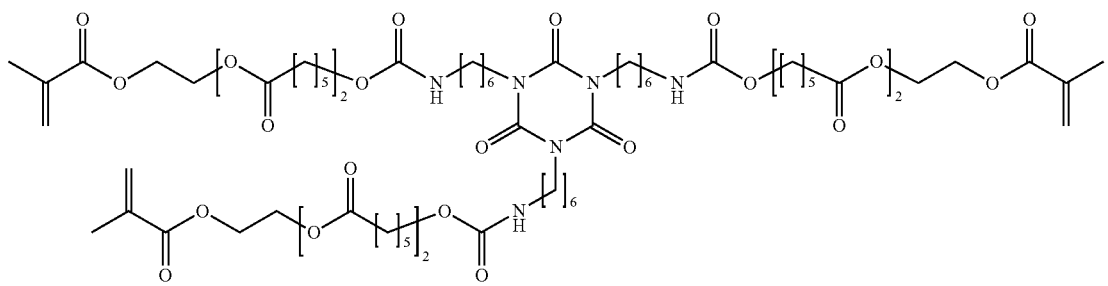

-continued

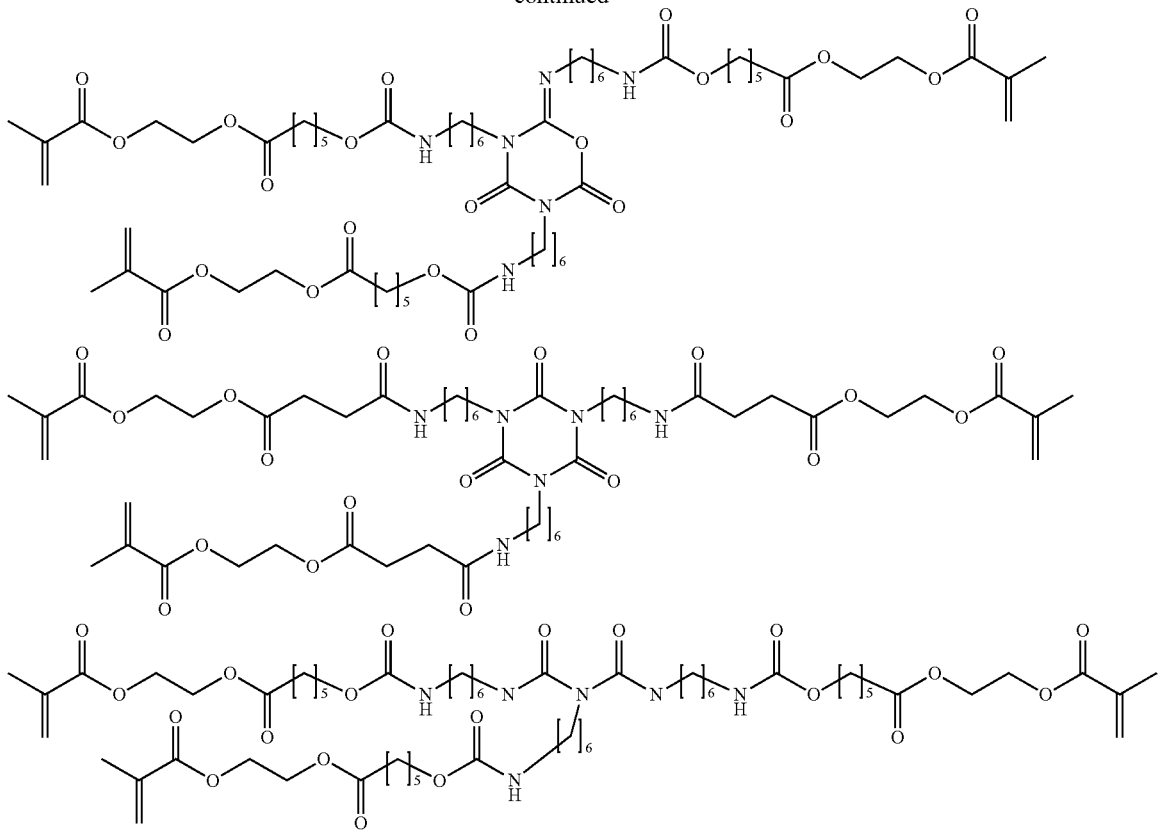

Further suitable urethane(meth)acrylates are based on α,ω-terminated poly(meth)acrylatdiols (e.g. as described in EP 1 242 493 B1) or can be a polyester, polyether, polybutadiene or polycarbonate urethane(meth)acrylate (e.g. as described in U.S. Pat. No. 6,936,642 B2).

The urethane(meth)acrylate is typically present in an amount of at least 1 or at least 3 or at least 4.5 wt. % with respect to the weight of the preformed dental composite crown.

The urethane(meth)acrylate is typically present in an amount of utmost 20 or utmost 15 or utmost 10 wt. % with respect to the weight of the preformed dental composite crown.

Thus, the urethane(meth)acrylate is typically present in an amount from 1 to 20 or from 3 to 15 or from 4.5 to 10 wt. % with respect to the weight of the preformed dental composite crown.

If the amount of urethane(meth)acrylate is too high, the resulting material might become too flexible and will probably not maintain its anatomical shape.

If the amount of urethane(meth)acrylate is too low, the resulting material might become too brittle and fracture work and impact strength might be negatively affected, The resin of the chemical composition also comprises a (meth)acrylate(s) having at least 1 or 2 polymerizable moieties but not comprising a urethane moiety.

Thus, the (meth)acrylate(s) is different from urethane (meth)acrylate, e.g. with respect to functionality, chemical moieties, molecular weight or combinations thereof.

If desired, the chemical composition may comprise at least two, three or four different kinds of (meth)acrylate(s).

Adding a (meth)acrylate to the resin composition helps to further improve the mechanical properties of the resin composition in its cured stage, in particular with regards to flexural strength or abrasion resistance.

The molecular weight of the (meth)acrylate(s) is typically at least 170 or at least 200 or at least 300 g/mol.

The molecular weight of the (meth)acrylate(s) is typically in a range from 170 to 3,000 or from 200 to 2,500 or from 300 to 2,000 g/mol.

The (meth)acrylate(s) has free radically active functional groups and includes monomers, oligomers, and polymers having two or more ethylenically unsaturated groups.

Such free radically polymerizable materials include di- or poly-acrylates and methacrylates such glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyl-dimethylmethane; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as diallyl phthalate, divinyl succinate, divinyl adipate and divinylphthalate.

Preferred ethylenically unsaturated monomers are methacrylate and acrylate monomers, such as di(meth)acrylates of propanediol, butanediol, hexanediol, octanediol, nonanediol, decanediol and eicosanediol, di(meth)acrylates of ethylene glycol, of polyethylene glycols and of polypropylene glycols, di(meth)acrylates of ethoxylated bisphenol A, for example 2,2'-bis(4-(meth)acryloxytetraethoxyphenyl)propanes, and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8 (9)-tricyclo[5.2.1.0$^{2,6}$]decylmethyl triglycolate. Particularly suitable are 2,2-bis-4(3-methacryloxy-2-hydroxypropoxy) phenylpropane (Bis-GMA), 2,2-bis-4(3-methacryloxypropoxy)phenylpropane, triethylene glycol dimethacrylate (TEGDMA), and di(meth)acrylates of bishydroxymethyltricyclo-(5.2.1.0$^{2,6}$)decane It was found that using (meth)acrylate(s) and more particularly, the components described above, can be beneficial to provide the hardened composition with sufficient mechanical strength as it may function as a kind of cross-linking agent useful to improve the mechanical properties of the cured dental composition.

The (meth)acrylate(s) is typically present in an amount of at least about 5 or at least about 10 or at least about 15 wt. % with respect to the weight of the whole composition.

The (meth)acrylate(s) is typically present in an amount of utmost about 60 or utmost about 50 or utmost about 45 wt. % with respect to the weight of the preformed dental composite crown.

Thus, the (meth)acrylate(s) is typically present in an amount from 5 to 60 or from 10 to 50 or from 15 to 45 wt. % with respect to the weight of the whole composition.

The chemical composition of the preformed dental composite crown may also comprise one or more additive(s).

Adding x-ray visible particles to the dental composition is beneficial in that it enables the practitioner to better identify the dental material in the mouth of a patient and distinguish between sound dental tooth structure and the dental restoration material. The dental material becomes radiopaque.

Radio-opacity of a dental material is advantageous in certain instances where X-rays are used to diagnose a dental condition. For example, a radiopaque material would allow the detection of secondary caries that may have formed in the tooth tissue surrounding a filling. The desired degree of radio-opacity can be varied, depending upon the particular application and the expectations of the practitioner evaluating the X-ray film.

Suitable x-ray visible particles include particles of metal oxides and metal fluorides. Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. Yttriumtrifluoride and Ytterbiumtrifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. Other suitable fillers to increase radiopacity are salts of barium and strontium especially strontium sulphate and barium sulphate.

The heavy metal oxide or metal fluoride particles may be surface treated.

If present, x-ray visible particles are typically present in an amount from 0.1 to 15 or from 1 to 10 or from 2 to 5 wt. % with respect to the weight of the whole composition.

Further additives, which can be optionally added, include anti-microbial(s), pigment(s), dyes, stabilizer(s) and fluoride releasing materials.

Examples of pigment(s) and dye(s), which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual colouring of the dental compositions.

Examples of fluoride release agent(s) which can be present include naturally occurring or synthetic fluoride minerals. These fluoride sources can optionally be treated with surface treatment agents.

Further additives, which can be added, include stabilizer(s), especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4', 6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers).

There is no absolute need for these additives to be present, so no additive(s) might be present at all. However, if they are present they are typically present in an amount which is not detrimental to the intended purpose.

Useful amounts for additive(s) include:

at least about 0.1 wt. % or at least about 0.5 wt. % or at least about 1 wt. % and/or up to about 15 wt. % or up to about 10 wt. % or up to about 5 wt. %.

Typical ranges include from 0.1 wt-% to 15 wt. % or from 0.5 wt. % to 10 wt. % or from 1 wt. % to 5 wt. %.

According to one embodiment the chemical composition of the preformed dental composite crown is described as follows:

Nano-filler(s): from 20 to 70 wt.-%,

Urethane(meth)acrylate(s): from 3 to 20 wt. %, (Meth)acrylate(s) not comprising a urethane moiety: from 5 to 60 wt. %.

According to another embodiment the chemical composition of the preformed dental composite crown is described as follows:

Nano-filler(s): from 30 to 55 wt. %,

Urethane(meth)acrylate(s): from 5 to 15 wt. %, (Meth)acrylate(s) not comprising a urethane moiety: from 10 to 50 wt. %.

According to one embodiment, the invention is also directed to a dental composite crown as described in the present text with a particular shape and being composed of a particular chemical composition:
the shape being characterized as follows:
for molars and premolars having a occlusal top surface and depending buccal, mesial, distal and lingual, respectively palatinal side surfaces,
for anterior teeth and incisors having a distal top surface and depending labial, mesial, distal and lingual, respectively palatinal side surfaces,
the side surfaces being connected to each other and forming a crown cervix,
the wall thickness of the crown at the crown cervix being from 0.1 to 0.4 mm, or from 0.1 to 0.3 mm,
wall thickness of the top surface being from 0.15 mm to 1.5 mm,
at least two of opposing depending side surfaces having a concave shape resulting in an undercut design larger than 0.2 mm or larger than 0.3 mm,
the chemical composition of the material the preformed dental composite crown is made of being a hardened composition and being characterized by comprising the following components:
nano-filler(s) in an amount from 20 to 60 wt. %,
resin matrix in an amount from 20 to 75 wt. %,
the resin matrix comprising the polymerization product of
urethane(meth)acrylate(s) having at least 2 polymerizable moieties in an amount from 3 to 20 wt. % and
(meth)acrylate(s) having at least 2 polymerizable moiety but not comprising a urethane moiety in an amount from 5 to 55 wt. %,
wt. % with respect to the weight of the chemical composition,
the hardened chemical composition being characterized by the following parameters:
impact strength: from 5 to 15 kJ/m$^2$ determined according to DIN 53453:175-05,
E-modulus: from 1,000 to 4,000 MPa determined according to ISO 4049:2009 in combination with DIN EN 843-2:2007.

The chemical composition described in the present text does typically not comprise components selected from
polymerizable component comprising an acidic group e.g. in an amount above about 5 wt. %,
solvent e.g. in an amount above about 5 wt. %,
filler particles having a mean particle size from 1 to 100 μm e.g. in an amount above about 10 wt. % or above about 5 wt. %,
and mixtures thereof; wt. % with respect to the weight of the preformed dental composite crown.

That is, those components are typically not willfully added and thus are not present in an amount above about 10 or above about 8 or above about 5 or above about 2 wt. % with respect to the weight of the whole composition.

However, depending on the raw materials chosen, it may sometimes be unavoidable that the composition may contain traces of either of the above components.

Adding filler having a mean particle size in the above mentioned range in an amount above about 10 wt. % may negatively influence properties like polishability and gloss retention.

Examples of such kind of fillers include fluoroaluminosilicate glasses, quartz, ground glasses, non-water-soluble fluorides such as $CaF_2$, cristobalite, calcium silicate, zeolites, including the molecular sieves, metal oxide powders, such as aluminium or zirconia or their mixed oxides, barium sulphate, calcium carbonate.

Adding such a filler in a high amount may negatively influence the aesthetic properties of the hardened dental composition.

Examples of solvents which are typically not present include linear, branched or cyclic, saturated or unsaturated alcohols, ketones, esters or mixtures of two or more of said type of solvents with 2 to 10 C atoms, like methanol, ethanol, iso-propanol, n-propanol, THF, acetone, methylethyl ketone, cyclohexanol, toluene, alkanes and acetic acid alkyl esters.

All components used in the chemical composition described in the present text should be sufficiently biocompatible, that is, the chemical composition should not produce a toxic, injurious, or immunological response in living tissue.

The preformed dental composite crown described in the present text can be obtained by using different technologies for production including additive manufacturing, molding and milling procedures.

In all these cases a hardenable composition is used containing
nano-filler(s) as described in the present text,
urethane(meth)acrylate(s) having at least 2 polymerizable moieties as described in the present text,
polymerizable (meth)acrylate(s) not comprising a urethane moiety as described in the present text,
initiator system suitable to cure the urethane(meth)acrylate(s) and (meth)acrylate(s),
optionally additives as described in the present text.

The initiator system which can be used for curing the chemical composition of the preformed dental composite crown described in the present text is not particularly limited but typically triggered by either radiation, heat, combining an oxidizing and reducing agent (often also referred to as redox curing initiator system) or a combination thereof.

The initiator system can be a one-component system (e.g. radiation or heat triggered initiators) or a two component system (e.g. combination of oxidizing and reducing agent).

One class of initiators capable of initiating polymerization of free radically active functional groups includes conventional chemical initiator systems such as a combination of an organic peroxide and an amine. These initiators, which rely upon a redox reaction, are often referred to as "auto-cure catalysts." They are typically supplied as two-part systems in which the reactants (reducing and oxidizing agent) are stored apart from each other and then combined immediately prior to use.

Organic peroxide compounds together with so-called activators are also suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451). Preferred malonyl sulfamides are 2,6-dimethyl-4-isobutylmalonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is preferably carried out in the presence of heavy-metal compounds and ionogenic halogen or pseudohalogen.

The heavy metal is suitably used in the form of soluble organic compounds.

Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

For shelf-life reasons the oxidizing and reducing agents of a redox curing initiator system are typically stored separately.

According to one embodiment, the chemical composition of the preformed dental composite crown is cured by a dark curing redox initiator system.

According to another embodiment, the chemical composition of the preformed dental composite crown is cured by a light curing initiator system.

Such initiators typically can be capable of generating free radicals for polymerization upon exposure to light energy having a wavelength between 400 and 800 nm.

Examples of visible light curing initiator components include for example systems based on an amine and an alpha-diketone. Suitable systems are described e.g. in U.S. Pat. No. 4,071,124 and WO 2009151957. The content of these references is herewith incorporated by reference.

Alternatively, free-radical initiators which can be used include the class of acylphosphine oxides, as described in U.S. Pat. No. 4,737,593. Such acylphosphine oxides are of the general formula

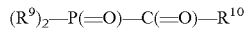

$(R^9)_2-P(=O)-C(=O)-R^{10}$ wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines include ethyl 4-(N,N-dimethylamino)benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethyl amino)-1-(4-morpholinophenyl)-1-butanone (IRGACURE™ 369, Ciba Specialty Chemicals), bis(η5-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

According to another embodiment, the chemical composition of the preformed dental composite crown is cured by a combination of redox initiator system and light curing initiator system.

In a further alternative, heat may be used to initiate the hardening, or polymerization, of free radically active groups. Examples of heat sources suitable for the curable resin composition described in the present text include inductive, convective, and radiant. Thermal sources should be capable of generating temperatures of at least 40° C. to 150° C. under normal conditions. This procedure is preferred for initiating polymerization of materials occurring outside of the oral environment. Suitable initiators which can be used and which are sensitive to heat are e.g. organic peroxides.

According to one embodiment, the preformed dental composite crown is produced by applying an additive manufacturing technology.

For this kind of technology, using an initiator system which is triggered by radiation was found to be useful.

The preformed dental composite crown can be obtained by a process comprising the steps of:
  providing a curable chemical composition, the curable chemical composition comprising the components of the chemical composition of the preformed dental composite crown and an initiator system being suitable to cure the curable chemical composition—as described in the present text,
  processing the curable chemical composition as construction material in an additive manufacturing process.

An example of this kind of technology is further described in U.S. Pat. No. 8,003,040 B2 (El-Siblani) relating to a process for producing a 3-dim object by solidifying layers with electromagnetic radiation of synergistic stimulation in a pattern. The content of these references is herewith incorporated by reference.

Using an additive manufacturing technology for producing the preformed dental composite crowns can be useful, if either small or large amounts of preformed dental composite crowns having different shapes need to be produced.

According to one embodiment, the preformed dental composite crown is produced by applying a molding technology.

For this kind of technology, all kinds of initiator systems can be used.

The preformed dental composite crown can be obtained by a process comprising the steps of:
  providing a curable chemical composition, the curable chemical composition comprising the components of the chemical composition of the preformed dental composite crown and an initiator system being suitable to cure the curable chemical composition—as described in the present text,
  molding the curable chemical composition into a mold having the shape of a the preformed dental crown to be produced, curing the chemical composition to obtain a cured preformed dental composite crown.

The curing of the curable chemical composition can be initiated by applying heat, radiation, using a redox-curing system or a combination thereof.

Using a molding technology for producing the preformed dental composite crowns can be useful, if large quantities of preformed and standardized dental composite crowns need to be produced.

According to another embodiment, the preformed dental composite crown is produced by applying a milling technology.

For this kind of technology, all kinds of initiator systems can be used, as well.

The preformed dental composite crown can be obtained by a process comprising the steps of:
  providing a composite milling block, the composite milling block having the chemical composition as described in the present text,
  milling an article out of the composite milling block, the article having the shape of the preformed dental composite crown described in the present text.

The composite milling block can be manufactured using the molding technique described above.

Using a milling technology for producing the preformed dental composite crowns can be useful, if only small quantities of preformed dental composite crowns need to be produced or if the production should be done "chair-side", that is by the dental practitioner during the treatment of a patient.

However, using a milling technology is not always recommended, in particular due to geometrical restrictions of the shape of the desired article (e.g. large undercuts).

The invention is also directed to a kit of parts comprising a set of preformed dental composite crowns as described in the present text.

The preformed dental composite crowns are typically distinguished from each other by either of the following: shape, color, size or a combination thereof.

A kit can comprise up to 10 or up to 8 differently shaped preformed dental composite crowns.

A kit can comprise each of the differently shaped preformed dental composite crowns in an amount up to 10 or up to 8 different sizes.

Thus, a kit can comprise up to 100 preformed dental composite crowns.

The preformed dental composite crowns can have the shape of an antherior or posterior or molar tooth.

Typically, the preformed dental composite crowns are provided in different tooth colours. Tooth colours are typically classified according to the Vita' colour code.

The kit of parts can also comprise a dental cement suitable for securely fixing the preformed dental composite crown to a prepared tooth surface.

Suitable dental cements are glass ionomer cements and in particular resin modified glass ionomer cements. Glass ionomer cements typically contain the following components: acid-reactive filler, polyacid, water, and complexing agent, but no radiation curable components.

Glass ionomer cements are typically provided as a kit of part comprising a liquid part and a powder part. The two parts have to be mixed before use.

The powder part typically comprises an acid-reactive inorganic filler (e.g. a fluoro alumosilicate glass, FAS glass).

The liquid part typically comprises a polyacid, water and a complexing agent (e.g. tartaric acid).

Glass ionomer cements are commercially available (e.g. Ketac™ Cem; 3M Oral Care; 3M ESPE).

The glass ionomer cement can also be provided as a kit of parts comprising two pastes A and B to be mixed before use.

According to a preferred embodiment, the kit of parts containing the preformed dental composite crowns comprises a resin modified glass ionomer cement (RM-GIZ).

Resin modified glass ionomer cements typically contain the following components: acid-reactive filler, polyacid, water, complexing agent, radiation curable components, initiator.

Suitable radiation curable components typically contain (meth)acrylate moieties.

Resin modified glass ionomer cements are provided as kit of parts as well, either as powder/liquid system or paste/paste system.

The powder part typically comprises acid-reactive inorganic filler(s) (e.g. a fluoro alumosilicate glass, FAS glass) and initiator components.

The liquid part typically comprises polyacid, water, (meth)acrylates and initiator components.

Resin modified Glass ionomer cements are commercially available (e.g. Ketac™ Cem Plus; 3M Oral Care; 3M ESPE).

It was surprisingly found that in particular a RM-GIZ is suitable for securely fixing the preformed dental composite crown to the surface of a prepared tooth.

Even, if a little bit more expensive than classical glass ionomer cements, RM-GIZ can be obtained at a lower expense compared to self-adhesive resin cements (e.g. RelyX™ Unicem or adhesive resin cements (e.g. RelyX™ Ultimate).

The preformed dental composite crown described in the present text is used for treating a dental tooth, in particular in the pediatric field.

Such a method comprises the step of fixing the preformed dental composite crown as described in the present text to the surface of a prepared tooth in the mouth of a patient by using a dental cement as described in the present text, in particular a resin modified glass ionomer cement.

If desired, the surface of the preformed dental composite crown which is to be attached to the surface of the prepared tooth ("inner surface") can be roughened before the dental cement is applied. Roughening can be done e.g. sandblasting.

Roughening the surface can be useful to even further improve the fixation of the preformed crown to the prepared surface of the tooth to be treated.

If desired, the shape of the preformed dental composite crown can be further adapted by a cutting or grinding.

The complete disclosures of the patents, patent documents, and publications cited in this text are incorporated by reference in their entirety as if each were individually incorporated.

The following examples are given to illustrate the invention.

EXAMPLES

Unless otherwise indicated, all parts and percentages are on a weight basis, all water is de-ionized water and all molecular weights are weight average molecular weight.

Moreover, unless otherwise indicated all experiments were conducted at ambient conditions.

Measurements Methods

Flexural Strength

If desired, flexural strength can be determined by conducting a three point flexural strength test according to ISO 4049:2009 using test specimen having the size 2*2*25 mm. Flexural strength is given in [MPa].

E-Modulus

If desired, the E-Modulus can be determined with a flexural strength measurement according to ISO 4049:2009 in combination with DIN EN 843-2:2007 using test specimen having the size 2*2*25 mm. The E-Modulus is determined between the range of 20% and 50% of the maximum force of the test specimen. E-Modulus is given in [GPa].

Impact Strength

If desired, the impact strength can be determined according to DIN 53453:1975-05 (Charpy) using test samples having the dimensions 4*6*50 mm, using a Zwick 5102 pendulum set up with a 0.5 J pendulum and using a span of 42 mm. Impact strength is given in [kJ/m2].

Abrasion

If desired, abrasion [mm$^3$] can be determined as follows: Abrasion tests were performed at specific specimens with a slope of 30°. For that purpose the materials were filled into the depression of M12 Inbus-screws and cured according to the manufacturers' instructions.

The specimens were flat grinded using a 75 µm diamond saw and stored in distilled water for 4 days at 36° C. Then chewing simulation was started applying the following conditions:

Chewing force: 80 N; Lateral movement: 4 mm; Sliding movement: 10 mm; Antagonist: steatite ball; Number of chewing cycles: 1,200,000; Thermocycles (5/55° C.): 5,000.

After conducting the chewing simulation abrasion was determined by measuring the loss of volume using a laser scanning microscope VK-X200 (Keyence Company).

Further information about the abrasion test can be found in M. Rosentritt et al., Materialprüfung 39 (1997), p. 77-80.

Crown Design:

A molar 3M Oral Care, 3M ESPE stainless steel crown (type: ELR-3/#N704922) was used as starting point for the design of a new preformed dental composite crown. The wall thickness of the stainless steel crown is essentially homogeneously (about 150 µm).

The inner surface of that stainless steel crown was scanned with a dental scanner (Lava™ Scan ST 2) and the wall thickness was homogenously scaled up with a CAD software (3-matic, Base 6.0-Software, build 6.0.0.13, Fa. Materialize N.V.) to about 300 µm to the outer direction. The inner surface of the crown design was left constant in order to ensure the same fit to a tooth stump.

The design of the crown was prepared for milling by calculation the milling strategy using a CAM Software (Lava™ Design Software 7 (Configuration C), Version: 3.2.1.256—14 Jun. 2018).

The design of the tested crowns is shown in FIG. 3.

Milling Block Preparation

Chemical Composition

The following components were provided and mixed using a kneader to obtain Paste A and Paste B.

Formulation (I)

| Component | Paste A Weight % | Component | Paste B Weight % |
|---|---|---|---|
| Zr/Si Nanocluster | 42.87 | HDK H-2000 | 10.0 |
| Aerosil R 711 | 1.0 | Z-Acetate | 79.7 |
| SG-YBF100 | 2.13 | BZPBS | 10.0 |
| HDK H-2000 | 4.0 | TBPIN | 0.3 |
| D-Zethacrylate | 44.797 | | |
| DESMA | 4.98 | | |
| Copper-procetonate | 0.003 | | |
| Amine-HCl | 0.19 | | |
| Ionol | 0.03 | | |
| Total: | 100 | Total: | 100 |

Formulation (III)

| Component | Paste A Weight % | Component | Paste B Weight % |
|---|---|---|---|
| Zr/Si Nanocluster | 42.87 | HDK H-2000 | 10.0 |
| Aerosil R 711 | 1.0 | Z-Acetate | 79.7 |
| SG-YBF100 | 2.13 | BZPBS | 10.0 |
| HDK H-2000 | 4.0 | TBPIN | 0.3 |
| D-Zethacrylate | 49.777 | | |
| DESMA | 0 | | |
| Copper-procetonate | 0.003 | | |
| Amine-HCl | 0.19 | | |
| Ionol | 0.03 | | |
| Total: | 100 | Total: | 100 |

Formulation (IV)

| Component | Paste A Weight % | Component | Paste B Weight % |
|---|---|---|---|
| Zr/Si Nanocluster | 42.87 | HDK H-2000 | 10.0 |
| Aerosil R 711 | 1.0 | Z-Acetate | 79.7 |
| SG-YBF100 | 2.13 | BZPBS | 10.0 |
| HDK H-2000 | 4.0 | TBPIN | 0.3 |
| D-Zethacrylate | 44.797 | | |
| DESMA | 0 | | |
| TEGDMA | 4.98 | | |
| Copper-procetonate | 0.003 | | |
| Amine-HCl | 0.19 | | |
| Ionol | 0.03 | | |
| Total: | 100 | Total: | 100 |

Abbreviations:

| NAME | Description | Availability |
|---|---|---|
| Zr/Si Nanocluster | aggregated nanoparticles | U.S. Pat. No. 6,730,156 B1, column 25, Preparatory Example A; the obtained filler particles were surface treated according to Preparatory Example B of U.S. Pat. No. 6,730,156 B1. |

-continued

| NAME | Description | Availability |
| --- | --- | --- |
| Aerosil™ R 711 | fumed silica (agglomerated nanoparticles) | Evonik |
| SG-YBF100 | ytterbium fluoride powder | |
| HDK H-2000 | silane treated fumed silica (agglomerated nanoparticles) | Wacker |
| D-Zethacrylate | ethoxylated Bisphenol A dimethacrylate | |
| DESMA | urethane(meth)acrylate | Example 1 of EP 2 167 013 B1 (page 20) |
| Copper-procetonate | Copper(II) bis(1-phenylpentan-1,3-dione) complex | |
| Amine-HCl | dibutylphenylethyl-amine hydrochloride | |
| Ionol | 2,6-ditert•butyl-4-methylphenol | |
| Z-Acetate | ethoxylated Bisphenol A diacetate | |
| BZPBS | 1-Benzyl-5-phenyl-barbituric acid | |
| TBPIN | tert•Butylperoxy-3,5,5-trimethylhexanoate | |
| TEGDMA | Triethylenglycole dimethacrylate | |

The pastes were filled in a dual chamber cartridge with a volume ratio of Paste A to Paste B of 10:1 (SulzerMixpac).

Preparation of Milling Blocks (I), (III) and (IV)

The respective compositions were dispensed through a static mixing tip (SulzerMixpac) by using a manually driven gear into a block mold (dimensions: 18 mm*14 mm*12 mm) made of silicon material (Fa.Siladent, Adisil® blau 9:1). The blocks were deformed after 3:30 min, cleaned with isopropanol, and stored afterwards in de-ionized water for 12 hours at 40° C. in an oven to finalize curing. The blocks were removed and dried with a paper towel.

Preparation of Milling Block (II)

A commercially available CAD/CAM material based on the thermoplastic material polyetheretherketon—PEEK was used (breCAM BioHPP Fa. Bredent/#420121). The material was sliced into dimensions of (18 mm*14 mm*12 mm).

Manufacturing of Preformed Crowns

Milling Blocks (I), (II), (III) and (IV) were glued into a milling machine holder (Lava™ Frame) using a glue (DELO Automix 03 rapid).

Crown (I) with a 300 µm wall thickness crown design—as described above—was milled from Milling Block (I) using a dry milling machine (Lava™ CNC 500-H004).

Crown (II) with a 300 µm wall thickness crown design—as described above—was milled from Milling Block (II) using a dry milling machine (Lava™ CNC 500-H004).

Crown (III) with a 300 µm wall thickness crown design—as described above—was milled from Milling Block (III) using a dry milling machine (Lava™ CNC 500-H004).

Crown (IV) with a 300 µm wall thickness crown design—as described above—was milled from Milling Block (IV) using a dry milling machine (Lava™ CNC 500-H004).

The inner surfaces of Crowns (I), (II), (III) and (IV) were roughened by sandblasting with $Al_2O_3$ powder.

Preparation of Tooth

An artificial tooth (Frasaco™ AK-6/2 ZE-85) was prepared on a tooth model (Frasaco™ AK-6/2) following the preparation guidelines suggested by the manufacturer of the 3M Oral Care, 3M ESPE stainless steel crowns.

Snap-on Test

The fit of Crowns (I) and (II) on the prepared tooth stump was tested manually. Both crowns had sufficient flexibility and showed the desired snap-on behaviour to the prepared tooth.

Testing of Pull-Off Force

Figure 4:
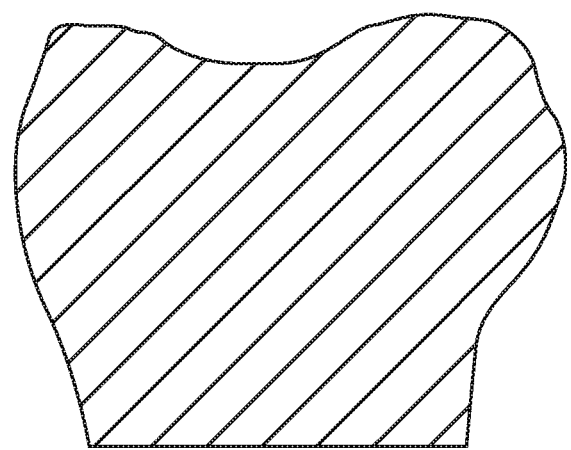
FIG. 4 shows the shape of a prepared artificial tooth in cross section.

An additional artificial tooth was prepared from brass by dry milling following the preparation guidelines suggested by the manufacturer of the 3M Oral Care, 3M ESPE stainless steel crowns. The cross section of the prepared tooth is shown in FIG. 4.

The surface of the artificial tooth was roughened by sandblasting using $Al_2O_3$ powder to ensure better bonding to the stump.

The following crowns were compared: Crowns (I), (II), (III) and (IV); in a group of 5 crowns each.

The crowns were cemented on the artificial tooth using the following commercially available dental cements according to the instruction of use provided by the manufacturer and stored at 37° C. under humid conditions for 24 h: Resin modified glass ionomer cement: Ketac™ Cem plus (3M Oral Care, 3M ESPE).

A brass pull off holder was cemented to the assembly (artificial tooth and cemented crown) on the occlusal area of the crown by using adhesive cementation technique (Rely™ X Unicem, 3M Oral Care, 3M ESPE).

The assembly including the pull off fixture was placed into an Instron™ machine and the pull off force (in N) was measured with a tensile loading speed of 1 mm/min until fracture of the cementation occurred. The standard deviation is given in brackets.

Results

| Crown (I) | Crown (II) | Crown (III) | Crown (IV) |
| --- | --- | --- | --- |
| 465.18 (+/−56.88) | 143.36 (+/−22.70) | 296.85 (+/−182.63) | 381.29 (+/−85.19) |

Figure 5:
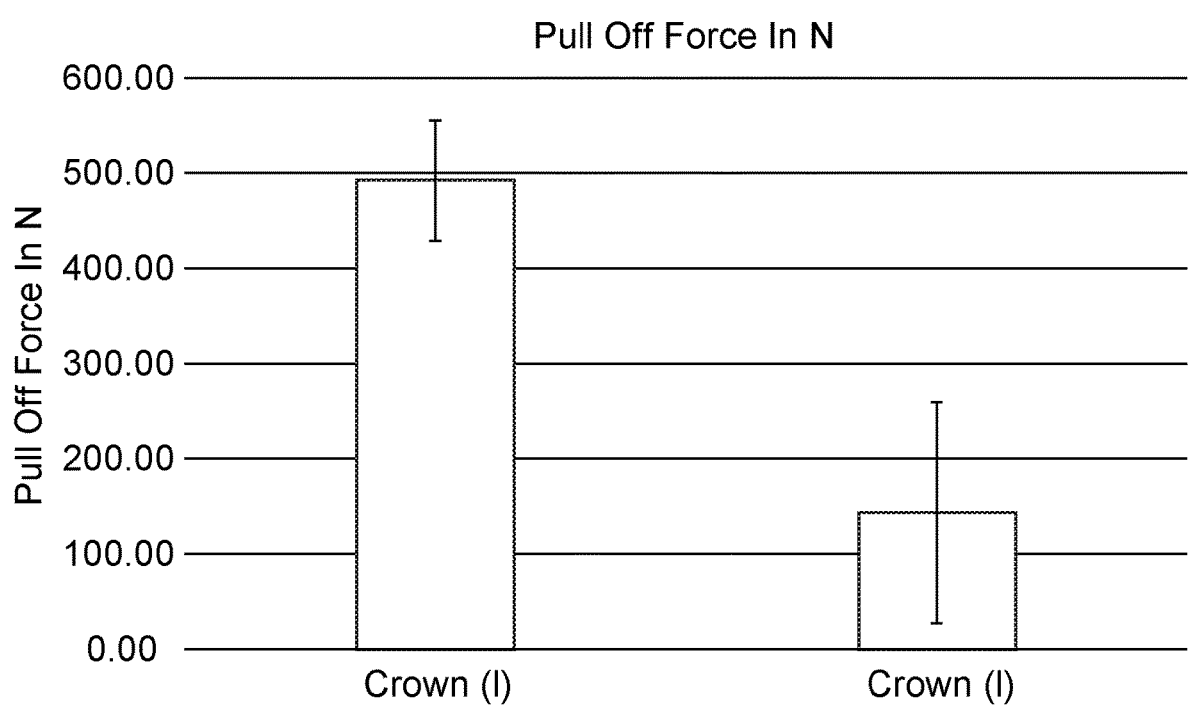
FIG. 5 shows a table with test results.

The results of the pull off test are also shown in FIG. 5.

The preformed dental composite crown as described in the present text (Crown (I)) showed better adhesion to the artificial tooth stump than the preformed dental crown made from the thermoplastic material PEEK suggested in U.S. Pat. No. 8,651,867 B2 (Zilberman)—Crown (II).

The preformed dental composite crown as described in the present text (Crown (I)) showed also better adhesion to the artificial tooth stump than the preformed dental crown made from Formulations (III) and (IV).

E-Modulus

In addition, the E-Modulus was determined (in GPa). The standard deviation is given in brackets.

Results

| Formulation (I) | Formulation (III) | Formulation (IV) |
| --- | --- | --- |
| 3.360 (+/−0.0679) | 3.500 (+/−0.178) | 3.630 (+/−0.144) |

The E-Modulus of the formulation (I) used for preparing the preformed dental composite crown as described in the present text (Crown (I)) was lower than the E-Modulus of the formulations (III) and (IV) used for preparing the preformed dental composite crowns (III) and (IV).

What is claimed is:

1. A preformed dental composite crown being characterized by its shape and chemical composition, the shape being characterized as follows:
for molars and premolars having an occlusal top surface and depending buccal, mesial, distal and lingual, respectively palatinal side surfaces,
for anterior teeth and incisors having a distal top surface and depending labial, mesial, distal and lingual, respectively palatinal side surfaces,
the side surfaces being connected to each other and forming a crown cervix,
the wall thickness of the crown at the crown cervix being lower than 0.6 mm;
at least two of opposing depending side surfaces having a concave shape;
the chemical composition of the material the preformed dental composite crown is made of being a hardened composition comprising the following components:
nano-filler(s) in an amount from 20 to 70 wt. %,
resin matrix in an amount from 20 to 75 wt. %,
wt. % with respect to the weight of the chemical composition,
the resin matrix comprising urethane(meth)acrylate(s) and (meth)acrylate(s) not comprising a urethane moiety.

2. The dental composite crown of claim 1, the shape being further characterized by at least one or more or all of the following features:
wall thickness of the side surfaces of the crown: not exceeding 0.6 mm;
wall thickness of the side surfaces of the crown: from 0.1 to 0.4 mm;
wall thickness of the top surface of the crown: from 0.15 mm and 1.5 mm;
undercut: more than 0.2 mm.

3. The dental composite crown of claim 1, the nano-filler(s) comprising particles of $SiO_2$, $ZrO_2$, $Al_2O_3$ or mixtures thereof.

4. The dental composite crown of claim 1, the nano-filler(s) comprising aggregated, agglomerated, discrete nano-sized particles or mixtures thereof.

5. The dental composite crown of claim 1, the urethane (meth)acrylate(s) being characterized as follows:
having the structure $A\text{-}(\text{-}S1\text{-}U\text{-}S2\text{-}MA)_n$, with
A being a connector element comprising at least one unit,
S1 being a spacergroup comprising at least 4 units connected with each other,
S2 being a spacergroup comprising at least 4 units connected with each other, the units of A, S1 and S2 being independently selected from $CH_3$—, —$CH_2$—, —O—, —S—, —$NR^1$—, —CO—, —$CR^1$=,

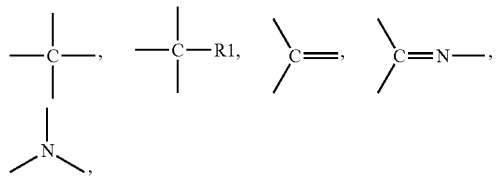

—N=, —$CR^1R^2$—,
with $R^1$ and $R^2$ being independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups,
U being a urethane group connecting spacergroups S1 and S2,
MA being an acrylate or methacrylate group and
n being 3 to 6.

6. The dental composite crown of claim 1, the (meth)acrylate(s) not comprising an urethane moiety being characterized as follows:
molecular weight being in a range from 170 to 3,000 g/mol,
comprising at least 2 polymerizable moieties.

7. The dental composite crown of claim 1, the chemical composition the dental composite crown is made of not comprising either or all of the following components:
polymerizable component(w) with an acidic group in an amount above 2 wt. %;
solvent(s) in an amount above 5 wt. %;
wt. % with respect to the weight of the dental composite crown.

8. The dental composite crown of claim 1, the chemical composition the dental composite crown is made of comprising:
Nano-filler(s) selected from aggregated, agglomerated or discrete nanoparticles and mixtures thereof in an amount from 20 to 70 wt. %,
Urethane(meth)acrylate(s) in an amount from 3 to 20 wt. %,
(Meth)acrylate(s) not comprising a urethane moiety in an amount from 5 to 55 wt. %,
wt. % with respect to the weight of chemical composition of the dental composite crown.

9. The dental composite crown of claim 1, the chemical composition the dental composite crown is made of being characterized by either of the following parameters or combinations thereof:
flexural strength: from 50 to 200 MPa or from 80 to 150 MPa determined according to ISO 4049:2009,
E-modulus: from 1,000 to 4,000 MPa determined according to ISO 4049:2009 in combination with DIN EN 843-2:2007;
impact strength: from 5 to 15 $kJ/m^2$ determined according to DIN 53453:175-05,
abrasion: less than about 20 or less than 15 or less than 10 $mm^3$,
color: being tooth colored.

10. The dental composite crown of claim 1, being characterized as follows:
the shape being characterized as follows:
for molars and premolars having an occlusal top surface and depending buccal, mesial, distal and lingual, respectively palatinal side surfaces,
for anterior teeth and incisors having a distal top surface and depending labial, mesial, distal and lingual, respectively palatinal side surfaces,
the side surfaces being connected to each other and forming a crown cervix,
the wall thickness of the crown at the crown cervix being from 0.1 to 0.4 mm,
wall thickness of the top surface being from 0.15 mm to 1.5 mm,
at least two of opposing depending side surfaces having a concave shape resulting in an undercut design larger than 0.2 mm, the chemical composition of the material the preformed dental composite crown is made of being a hardened composition and being characterized by comprising the following components:

nano-filler(s) in an amount from 20 to 70 wt. %,
resin matrix in an amount from 20 to 75 wt. %,
the resin matrix comprising the polymerization product of:
urethane(meth)acrylate(s) having at least 2 polymerizable moieties in an amount from 3 to 20 wt. % and
(meth)acrylate(s) having at least 2 polymerizable moiety but not comprising a urethane moiety in an amount from 5 to 55 wt. %,
wt. % with respect to the weight of the chemical composition,
the chemical composition being characterized by the following parameters:
impact strength: from 5 to 15 kJ/m$^2$ determined according to DIN 53453:175-05, E-modulus: from 1,000 to 4,000 MPa determined according to ISO 4049:2009 in combination with DIN EN 843-2:2007.

11. A kit of parts comprising a set of preformed dental composite crowns of claim 1, the preformed dental composite crowns being distinguished from each other by either of the following: shape, color, size or a combination thereof.

12. The kit of claim 11, comprising in addition a dental cement and a dental composite material.

13. The kit of claim 12, the dental cement being a resin modified glass ionomer cement, self-adhesive resin cement or adhesive resin cements.

14. A dental composite crown for use in a method of treating a dental tooth, the method comprising the step of fixing the dental composite crown of claim 1 to the surface of a prepared tooth in the mouth of a patient by using a dental cement.

15. A process of producing the preformed dental composite crown of claim 1, by either of the following methods:
applying an additive manufacturing technology,
applying a molding technology,
milling the preformed dental composite crown out of a milling block.

* * * * *